July 13, 1943. C. MALLERIN Plant Pat. 594
ROSE PLANT
Filed Jan. 19, 1943
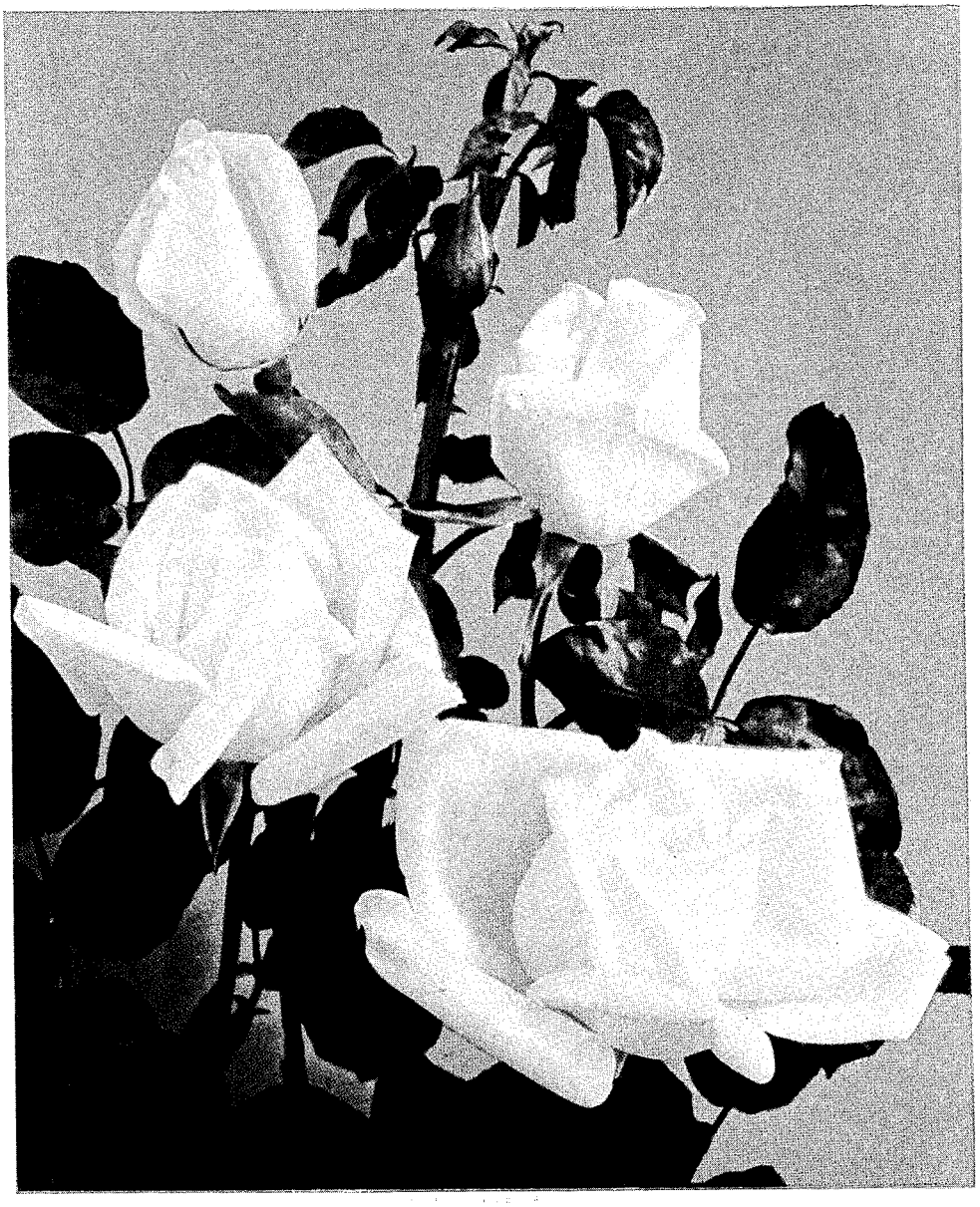
Inventor
Charles Mallerin
By Robb & Robb
Attorneys Patented July 13, 1943

UNITED STATES PATENT OFFICE

594

ROSE PLANT

Charles Mallerin, Varces, France, assignor to The Conard-Pyle Company, West Grove, Pa.

Application January 19, 1943, Serial No. 472,889

1 Claim. (Cl. 47—61)

The present invention relates to a new and distinct variety of rose plant, the result of definite efforts to obtain an improved type of white rose.

To this end I crossed two well known white varieties Edith Krause, more or less greenish white, and Mme. Louis Lens, a very attractive white rose, with the result that the present variety, a seeding of the cross represents something entirely new and superior in white roses. This superiority resides primarily in the form of the bud, the purity of color of the flowers, and the vigor of the plant constituting the most important introduction of white roses since that of the well known Kaiserin Auguste Viktoria some fifty years ago.

The characteristics of this new rose are set forth more specifically and extensively in the following detail description in which color terminology refers to Ridgway's Color Standard:

Type: Hardy; tall; outdoor; seedling; for cut flowers and garden decoration.
Class: Hybrid Tea.
Parentage:
*Seed parent.*—Edith Krause.
*Pollen parent.*—Mme. Louis Lens.
Propagation: Holds its distinguishing characteristics through succeeding propagations by budding, which is the only method employed up to the present time.

*Flower*

Locality where grown: West Grove, Pennsylvania.
Flowers borne: Singly and several to stem; on normal, medium stems.
Quantity of bloom: Free, outdoors.
Continuity: Intermittent.
Fragrance: Moderate; tea.
Bud:
*Peduncle.*—Medium length; medium heavy; erect; Lettuce-Green, Plate V; almost smooth; few prickles, Maroon, Plate I.
*Before calyx breaks.*—*Size*—medium. *Form*—ovoid with an inconspicuous neck, with foliaceous appendages on the surface of the bud, with stout much cut foliaceous parts extending beyond the tip of the bud equal to ¾ or more of its length.
*As calyx breaks.*—*Color*—Light Yellow-Green, Plate VI.
*As first petal opens.*—*Size*—medium. *Form*—ovoid. *Color*—outside—White; inside—White. *Opening*—opens up well.

Bloom:
*Size.*—When fully open, 3¾ to 4 inches.
*Petalage.*—Double; from thirty-five to forty arranged irregularly.
*Form.*—Full high center at first; becoming globular; petals remaining at first loosely cupped rolled outward; becoming later, at maturity, loosely rolled outward.
Petals: Soft, with inside satiny and outside satiny.
*Shape.*—Outside—obovate, with apex flat, with 1 notch. Intermediate—ovate, with apex flat, with 1 notch. Inside—ovate, with apex flat, with 1 notch.

This description of a newly opened flower was made from a rose grown outdoors, in the month of August, 1941, at West Grove, Pennsylvania:

*Color.*—Outside petal: outside surface—White; inside surface—White. Intermediate petal: outside surface—White; inside surface—White. Inner petal: outside surface—White; inside surface—White.

This description was made from a rose that was open for three days, outdoors, in the month of August, 1941, at West Grove, Pennsylvania:

*Color.*—Outside petal: outside surface—White; inside surface—White. Inside petal: outside surface—White; inside surface—White.
*General color effect.*—Newly opened flower—White. Three days open—White.
*Behavior.*—Drop off cleanly.
*Flower longevity.*—On bush in garden, three to four days in August. Cut roses grown outdoors, three to five days in August.

*Reproductive organs*

Stamens: Many; arranged regularly partly about pistils.
Filaments: Medium length; Pale Greenish-Yellow, Plate V, most with anthers.
Anthers: Medium size; Amber-Brown, Plate III, open at various times.
Pistils: Medium number.
Styles: Short; thin; bunched.
Stigma: Pomegranate Purple, Plate XII.
Ovaries: All enclosed in calyx.
Hips: Globular with inconspicuous neck, Oil-Green, Plate V; smooth; walls thick.

Sepals: Permanent; moderately long; recurved.
Seeds: Medium size.

*Plant*

Foliage:

*Leaves.*—Compound of 3, 5 leaflets; normal amount; medium size; leathery, glossy.

*Leaflets.*—Ovoid with apex acute; base obtuse; margin simply serrate.

*Color.*—*Matures* upper surface—Cedar-Green, Plate VI; under surface—Parrot-Green, Plate VI. *Young:* upper surface—Olive-Green, Plate XVI, flushed Garnet-Brown, Plate I; under surface—Garnet-Brown, Plate I, flushed Olive-Green, Plate XVI.

*Rachis.*—Upper side—smooth, grooved, slightly hairy. Under side—moderately prickly thorny.

*Stipules.*—Moderately long; moderately wide; with medium long points, turning out at an angle of less than 45°, recurved toward the stem.

*Disease.*—Resistant.

Growth:

*Habit.*—Bushy; upright; much branched.

*Growth.*—Vigorous.

*Canes.*—Medium heavy.

*Main stems.*—Dull Grass-Green, Plate VI. *Thorns*—several; hooked downward; with short narrow base. *Prickles*—none. *Hairs*—none.

*Branches.*—Dull Grass-Green, Plate VI. *Thorns*—hooked downward; with short narrow base. *Prickles*—none. *Hairs*—none.

*New shoots.*—Dull Brussels-Brown, Plate III. *Thorns*—medium length; hooked downward; with short narrow base. *Prickles*—none. *Hairs*—none.

I claim:

A new and distinct variety of rose plant, characterized as to novelty by its vigor of growth, the form and color of the bud, and the size, number of petals and the purity of the white color of its flowers, substantially as shown and described.

CHARLES MALLERIN.